United States Patent
Mellin et al.

(10) Patent No.: US 9,987,391 B2
(45) Date of Patent: Jun. 5, 2018

(54) INJECTABLE HYDROGELS

(71) Applicant: ST. JUDE MEDICAL COORDINATION CENTER BVBA, Zaventem (BE)

(72) Inventors: Lisa Mellin, Uppsala (SE); Niklas Borg, Storvreta (SE); Martina Källrot, Lidingö (SE)

(73) Assignee: ST. JUDE MEDICAL COORDINATION CENTER BVBA, Zaventem (BE)

( * ) Notice: Subject to any disclaimer, the term of this patent is extended or adjusted under 35 U.S.C. 154(b) by 480 days.

(21) Appl. No.: 13/800,013

(22) Filed: Mar. 13, 2013

(65) Prior Publication Data

US 2014/0277112 A1 Sep. 18, 2014

(51) Int. Cl.
| | | |
|---|---|---|
| *C08K 3/10* | (2018.01) | |
| *A61L 24/00* | (2006.01) | |
| *A61L 27/14* | (2006.01) | |
| *A61L 27/52* | (2006.01) | |
| *A61L 24/04* | (2006.01) | |
| *A61K 47/34* | (2017.01) | |

(52) U.S. Cl.
CPC .......... *A61L 24/0031* (2013.01); *A61K 47/34* (2013.01); *A61L 24/04* (2013.01); *A61L 24/046* (2013.01); *A61L 27/14* (2013.01); *A61L 27/52* (2013.01); *A61L 2430/36* (2013.01)

(58) Field of Classification Search
None
See application file for complete search history.

(56) References Cited

U.S. PATENT DOCUMENTS

| | | |
|---|---|---|
| 2009/0269417 A1 | 10/2009 | Gonzalez et al. |
| 2010/0297155 A1 | 11/2010 | Song et al. |
| 2011/0033503 A1 | 2/2011 | Sinko et al. |
| 2011/0033540 A1 | 2/2011 | Daniloff et al. |
| 2011/0218298 A1 | 9/2011 | Puskas et al. |

FOREIGN PATENT DOCUMENTS

| | | |
|---|---|---|
| EP | 2 597 110 A1 | 5/2013 |
| JP | 10-158195 A | 6/1998 |
| JP | 2011-173887 A | 9/2011 |
| WO | WO-2004/060346 A2 | 7/2004 |
| WO | WO 2010/087912 A1 | 8/2010 |
| WO | WO-2012/035598 A1 | 3/2012 |

OTHER PUBLICATIONS

Odriozola et al Gold-glutathione supramolecular hydrogels, J. Mater. Chem. 2007, 17, 4843-4845.*
I. Odriozola et al., Designing neutral metallophilic hydrogels from di- and tripeptides, *Organic & Biomolecular Chemistry*, vol. 9, No. 14, Jan. 1, 2011, pp. 5059-5031.
S. Choh et al., "Facile Synthesis and Characterization of Disulfide-Cross Linked Hyaluronic Acid Hydrogels for Protein Delivery and Cell Encapsulation", *Biomacromolecules*, vol. 12, No, 4, Apr. 11, 2011, pp. 1126-1136.
European Search Report dated Dec. 9, 2014, 10 pgs.
Japanese Office Action with Translation, Mar. 3, 2015, 8 pages.
Burdick, J. A., et al., "Hyaluronic Acid Hydrogels for Biomedical Applications", *Adv. Mater.*, vol. 23, (2011), pp. H41-H56.

* cited by examiner

*Primary Examiner* — Robert T Butcher
(74) *Attorney, Agent, or Firm* — Foley & Lardner LLP

(57) ABSTRACT

Described herein are methods of forming hydrogels comprising combining (a) a water-soluble polymer comprising thiol groups, and (b) a water-soluble metal salt in an aqueous solution. The hydrogels form rapidly. Hydrogels and related methods, uses, and products also are described.

8 Claims, No Drawings

INJECTABLE HYDROGELS

TECHNICAL FIELD

The present disclosure relates to injectable hydrogels, methods and kits for making them, and methods of using them.

BACKGROUND

Hydrogels are diluted polymer networks that are cross-linked and which contain, by weight, mostly a liquid, but behave like a solid material. The polymers of a hydrogel are hydrophilic, rendering the gel highly absorbent. Hydrogels have important applications in medical devices and implants, as well as in drug delivery vehicles.

There are documents disclosing systems for injectable hydrogels, wherein the injected composition comprises two or more parts which form a gel in situ when mixed.

WO 2010/087912 is directed to a composition comprising a polymer comprising thiol groups and gold nanoparticles which forms a hydrogel. The gel is said to be suitable for anchoring cells and growing cells in a 3-D matrix. The nanoparticles are described as clusters of gold atoms having a size of 0.5 to 250 nm, and the polymer is exemplified as a polysaccharide. Each nanoparticle is said to bind to several thiol groups and thereby act as a multivalent cross-linker. The gelling time for the system disclosed in WO2010/087912 is said to be from 24 to 48 hours.

There are documents that disclose the use of oxidizing substances such as oxygen and hydrogen peroxide to form disulphide crosslinkage from dithiol containing polymers. However, the use of oxygen or hydrogen peroxide in a large amounts brings a risk of explosion and fire, especially during heating. Use of these compounds may also be a hazard to a worker's health. Further, the use of hydrogen peroxide to oxidize two thiol groups may not stop at the formation of a disulphide but may cause further oxidation into a sulfonic acid which might degrade the polymer. Also, the formed acid is toxic both for people coming in contact with the material and the environment.

US 2011/0218298 discloses a method of forming disulphide-crosslinked gels by providing a composition of dithiol polymers and subjecting them to an oxidizing environment containing oxygen, hydrogen peroxide and a tertiary amine, where the amount of oxygen and hydrogen peroxide is low. Even though the inventors state that the reaction was faster, the gelling time was still reported to be around 16 hours. Further, in order to form the gels, organic solvents such as THF had to be used, which would not be suitable for injectable in situ forming gels.

US 2009/026417 discloses a method of forming a gel from thiolated chitosan using an oxidizing agent and/or an external crosslinking agent. The oxidizing agents are said to be hydrogen peroxide, oxygen, horseradish peroxidase or mushroom tyrosinase, and the external crosslinking agent are said to be a low molecular weight aldehyde such as genipin and glutaraldehyde. When using ultra low molecular weight chitosan modified with thiobutylamidine and hydrogen peroxide, a gel reportedly was formed in 5 minutes.

US 2011/0033503 is directed to a spray-on hydrogel of PEG polymers that are cross-linked in situ such that the cross-links are reversible. The PEG is said to be a multi-armed polymer, with for example 4 or 8 arms, having a sulfhydryl, a thiol or a mercaptan moiety, and is cross-linked using hydrogen peroxide or a maleimide or a thiopyridine terminated cross-linker. The gelation time when using the maleimide cross-linker was reported to be almost instant.

SUMMARY

Embodiments described herein include hydrogels, methods for producing hydrogels, kits for producing hydrogels, and methods and uses of hydrogels.

For example, some embodiments relate to a method for producing a hydrogel comprising combining (a) an aqueous solution comprising a water-soluble polymer comprising thiol groups, and (b) a water-soluble metal salt; and thereafter permitting the combination to form a hydrogel.

In accordance with any embodiments, the metal salt may be a gold salt, such as one or more of gold chloride, potassium tetrachloroaurate, potassium tetrabromoaurate, potassium tetraiodoaurate, sodium tetrachloroaurate, sodium tetrabromoaurate, sodium tetraiodoaurate, sodium thiosulfatoaurate, potassium gold cyanide (KAu(CN)$_2$), and combinations of one or more thereof, such as AuCl$_3$.

In accordance with any embodiments, the polymer may comprise a polymer backbone and, optionally, one or more of substituents and branches, wherein thiol groups are attached to one or more of the backbone, substituents, and branches. In some embodiments, the water-soluble polymer comprises a polyethylene glycol comprising at least 4 branches.

In accordance with any embodiments, the molar ratio of thiol groups to metal atoms may be from about 1000:1 to about 1:1.

In accordance with any embodiments, the hydrogel may form in less than about 60 seconds.

In accordance with any embodiments, the hydrogel may be biodegradable.

Also provided are hydrogels made by any of the processes described herein, and kits for making the hydrogels described herein.

Also provided are hydrogels comprising (a) a polymer comprising a polymer backbone and, optionally, substituents, branches, or both, wherein the polymer comprises thiol groups attached to one or more of the backbone, substituents, or branches; and (b) metal atoms to which the thiol groups are bound, wherein the hydrogel does not contain gold nanoparticles.

Also provided are vascular sealing materials, vascular closure devices, drug-delivery vehicles, and tissue engineering materials comprising a hydrogel as described herein.

Also provided are vascular closure devices comprising a housing, wherein the housing comprises a first compartment and a second compartment, wherein the first compartment holds a water-soluble polymer comprising thiol groups and the second compartment holds a water-soluble metal salt. In some embodiments, the vascular closure device further comprises a third compartment for combining the contents of the first and the second compartments.

DETAILED DESCRIPTION

Described herein are hydrogels, methods of producing hydrogels, kits for forming hydrogels, and methods and uses for hydrogels.

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Any suitable materials and/or methods known to those of ordinary skill in the art can be utilized in carrying out the present invention. However, specific materials and methods are described. Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein "subject" denotes any animal in need of treatment, including humans. For example, a subject may be suffering from or at risk of developing a condition that can be treated or prevented with a hydrogel as described herein.

Methods of Forming Hydrogels

In some embodiments, the present disclosure relates to a method for producing a hydrogel comprising combining a water-soluble polymer comprising thiol groups and a water soluble metal salt, and thereafter permitting the combination to form a hydrogel.

The Water Soluble Polymer

Water-soluble polymers useful in injectable hydrogels are known, and include biocompatible polymers that are generally safe for injection into subjects, including humans. As used herein, the term "water-soluble polymer" includes polymers that are soluble or partially soluble in water.

In some embodiments, the hydrogel is biodegradable and comprises a biodegradable water-soluble polymer. Suitable biodegradable polymers are known in the art and include polymers susceptible to biodegradation by any known means, for example by hydrolysis.

In accordance with any embodiments, the water soluble-polymer may comprise a polymer backbone and optionally one or more branches, substituents, or both. (In the present disclosure the terms "branch" and "arm" mean the same thing and are used interchangeably.) The polymer can have, for example, 1 or more, 2 or more, 3 or more, 4 or more, 5 or more, 6 or more, or 8 or more branches and/or substituents. Without being bound by theory, it is believed that an increased number of branches results in a more solid and stable gel with a reduced gelling time.

In accordance with any embodiments, the water-soluble polymer may have a molecular weight of about 1,000 g/mol or more, about 10,000 g/mol or more, about 20,000 g/mol, about 50,000 g/mol or more, or about 100,000 g/mol or more. In some embodiments, the water soluble polymer has a molecular weight of about 200,000 g/mol or less.

Exemplary water soluble polymers include, for example, one or more polysaccharides, such as hyaluronic acid, polyhyaluronic acid, or chitosan; gelatin; cellulose; starch; lipids; albumin; collagen; polylysine; polyvinyl alcohol; polyvinyl pyrrolidone; polyethylene glycol; polypropylene glycol; polyacrylic compounds; methacrylic compounds; polyethylene imines; polysiloxane; polyacrylamides; poly-ethylene oxide; poly(2-acrylamido-2-methyl-1-propanesulfonic acid); or copolymers thereof; oligomers of lactic acid, glycolic acid, paradioxanone, caprolactone, trimethylene carbonate, or co-oligomers thereof; oligomeric esters; small molecules; or any combination or mixture thereof.

As noted above, at least one water-soluble polymer has thiol groups. The number and position of thiol groups per polymer can be selected to control properties of the hydrogel. For example, a polymer may include 2 or more, 4 or more, 6 or more, 8 or more, 10 or more, 20 or more, 50 or more, 100 or more, 200 or more, or 300 or more thiol groups. The thiol groups can be attached anywhere on the polymer, for example, on the backbone of the polymer; on a branch or substituent of the polymer; on a terminus of the backbone, branch, and/or substituent (e.g., in an end-cap position), or in any permutation and combination of one or more such sites of attachment.

In some embodiments, the water-soluble polymer is provided in an aqueous solution. In some embodiments, the aqueous solution comprises water, for example distilled water, deionized water, reverse osmosis water, Milli-q™ water, or ordinary tap water. In some embodiments, the solution further comprises one or more other suitable solvents, preservatives, and the like.

The water-soluble polymer concentration in the aqueous solution can be selected and controlled to impact the rate of hydrogel formation. For example, the water-soluble polymer can comprise about 1% or more, about 3% or more, about 5% or more, or about 10% or more, by weight of the aqueous solution. In some embodiments, the water-soluble polymer concentration is about 20% or less, about 15% or less, or about 10% or less, by weight. In some embodiments, the polymer concentration is from about 1 to about 20 weight %.

The Water Soluble Metal Salt

In some embodiments, the water-soluble metal salt comprises a thiol-binding metal. The thiol-binding metal can be, for example, gold. In some embodiments, the salt is one or more of gold chloride, potassium tetrachloroaurate, potassium tetrabromoaurate, potassium tetraiodoaurate, sodium tetrachloroaurate, sodium tetrabromoaurate, sodium tetraiodoaurate, sodium thiosulfatoaurate, or potassium gold cyanide ($KAu(CN)_2$). In some embodiments, the gold chloride salt is $AuCl_3$. In some embodiments, the gold salt is a mixture of gold salts.

In some embodiments, the metal salt is provided in an aqueous solution, such as being dissolved in water or an aqueous medium, including any form of water discussed above. In some embodiments, the salt is at least partially dissociated into cations and anions. In some embodiments, the metal, for example gold, is not in nanoparticle or particle form.

The metal salt concentration in the aqueous solution can be selected and controlled to impact the rate of hydrogel formation and/or the degree of crosslinking. In some embodiments, the metal salt concentration is about 0.1% or more, about 0.3% or more, about 0.5% or more, about 1% or more, about 3% or more, about 5% or more, or about 10% or more, by weight, of the aqueous solution. In some embodiments, the metal salt concentration is about 40% or less, about 30% or less, about 15% or less, or about 10% or less, by weight. In some embodiments, the metal salt concentration is from about 0.05% to about 40% by weight of the solution.

Forming a Hydrogel

In some embodiments, the water-soluble metal salt is combined with the water-soluble polymer to form a hydrogel. In some embodiments, the molar ratio of thiol groups of the water-soluble polymer to metal atoms of the metal salt (for example gold atoms), e.g., the molar ratio of thiol groups to gold atoms, is from about 1000:1 to about 1:1, for example between about 500:1 to about 5:1, about 200:1 to about 10:1, about 100:1 to about 20:1, or about 60:1 to about 40:1.

In some embodiments, the water-soluble polymer is added to an aqueous solution of the metal salt. In other embodiments, the metal salt is added to an aqueous solution of the water-soluble polymer. In other embodiments, an aqueous solution of the water-soluble polymer is combined with an aqueous solution of the metal salt. In accordance with such embodiments, the volume ratio of the aqueous solutions can be selected and controlled based on the relative concentrations of the solutions, to impact the rate of hydrogel formation and/or the degree of crosslinking, and/or for convenience and ease of combining. In some embodiments the voluble ratio of the aqueous solution of the water-soluble polymer and the aqueous solution of the metal salt is from about 0.1:1 to about 10:1, for example from about 1:1 to about 8:1, from about 1:1 to about 5:1, or from about 2:1 to about 4:1.

In some embodiments, the method comprises permitting the combination to form a hydrogel, with or without active mixing. For example, upon combining, the water-soluble polymer and metal salt may form a hydrogel without active mixing. Alternatively, formation of the hydrogel is facilitated by active mixing, such as by shaking, stirring, or agitating.

While not wanting to be bound by any theory, in some embodiments of the hydrogels described herein, the metal atoms that are bound to thiol groups are not directly bound to other metal atoms. In some embodiments, a thiol group forms an ionic bond with a metal atom, for example a thiol group forms an ionic bond with a gold atom.

As noted above, the amount of time required for hydrogel formation can be selected and controlled based on the intended use of the hydrogel, method or kit, for example, whether the hydrogel is used as a drug delivery vehicle, tissue engineering material, or vascular closure material. In general, gelling time can be instantaneous or short, such as 1 minute or less. For example, the gelling time can be, 60 seconds or less, 30 seconds or less, 20 seconds or less, 10 seconds or less, 5 seconds or less, or 1 second or less. As noted above, gelling time can be altered by any suitable method, such as by altering the concentration of the water-soluble polymer and/or metal salt solutions, altering the molar ratio between the thiol groups and the metal salt, altering branches and/or substituents of the water-soluble polymer, and/or altering the water-soluble polymers used.

Optional Hydrogel Ingredient(s)

In some embodiments, one or more optional ingredient(s) are used in the hydrogel. For example, one or more optional ingredient(s) can be provided in the water-soluble polymer solution, in the water-soluble metal salt solution, in both, or in a separate solution that can be combined with one of the solutions prior to or simultaneously with combining with the other, or that can be combined with the combined solutions, for example, as or after the hydrogel forms.

In some embodiments, an optional ingredient is a component with tissue adhering or binding properties, for example succinimidyl glutarate or a peptide sequence such as RGD peptides. In some embodiments, a tissue adhering or binding component is provided as a substituent on the water-soluble polymer, such as an RGD substituent on the polymer. In other embodiments a tissue adhering or binding component is provided as a separate ingredient that is added to one or both of the water-soluble polymer solution, the water-soluble metal salt solution, or in a separate solution.

In some embodiments, the optional ingredient(s) include, for example, one or more therapeutic agents, antimicrobial agents, bioactive substances, or contrast agents, A therapeutic agent can be, for example, drugs, antifungal agents, hemostatic agents, anti-inflammatory agents, analgesics, chemotherapy agents, cytokines, vitamins or vasoconstrictors. A bioactive substance can be, for example, growth factors, such as BNP, VEGF and FGF; nucleic acids; peptides; or proteins.

In some embodiments, the optional ingredient(s) include, for example, buffering agents, or other pharmaceutically acceptable adjuvants. The buffering agents can be, for example, tensides, surfactants, glycine, potassium chloride, potassium phosphate, sodium acetate, sodium citrate, sodium phosphate, glycinamide, or their conjugate acids.

Without being bound by theory, it is believed that the instantaneous or rapid gelling achieved by the methods described herein can trap optional ingredient(s) inside the formed hydrogel. That is, the optional ingredient(s) may become trapped in the hydrogel matrix as the hydrogel forms. It is believed that this rapid entrapment can provide even distribution of the optional ingredient(s) throughout the hydrogel, and minimize the risk of burst release of optional ingredient(s).

Hydrogels

In some embodiments, the present disclosure relates to a hydrogel made by any of the methods disclosed herein. For example, the hydrogel can comprise (a) a polymer comprising a polymer backbone and optionally substituents, branches, or both, wherein the polymer comprises thiol groups attached to one or more of the backbone, substituents, or branches; and (b) a metal.

In some embodiments, the metal is gold. In some embodiments, at least some of the thiol groups are bound to gold atoms. In some embodiments, the gold atoms are not directly bound to any other gold atoms. In some embodiments, the hydrogel does not contain gold nanoparticles. In some embodiments, at least some of the thiol groups are attached to gold atoms via ionic bonding.

In some embodiments, the hydrogel comprises at least one polyethylene glycol comprising at least 4 branches.

Hydrogel Kits

In some embodiments, the present disclosure relates to a kit for forming a hydrogel as disclosed herein. The kit can comprise, for example, a first and a second component. The first component can comprise a water-soluble polymer comprising thiol groups as described above, optionally provided in an aqueous solution. The second component can comprise a water-soluble metal salt as described above, optionally provided in an aqueous solution. The first and second components can be provided in separate containers or separate compartments of a single container. In some embodiments, the kit can include a third container or compartment for combining the first and second components.

The kit may include instructions for combining the first and second components to form a hydrogel. The kit also may include instructions for using the hydrogel as an injectable hydrogel in a vascular closure device, for vascular closure, as a drug-delivery vehicle, and/or as a tissue engineering material.

Vascular Closure Devices

In some embodiments, the present disclosure relates to a vascular closure device. Exemplary vascular closure devices are described, for example, in U.S. patent application Ser. No. 13/770,586, filed Feb. 19, 2013, the entire contents of which are incorporated herein by reference in the entirety. For example, a vascular closure device can be used to deliver a volume of a sealant material, such as a hydrogel as described herein (or components thereof) to a vascular puncture, for sealing the puncture. In some embodiments, the device comprises a housing comprising a plurality of chambers, including a first chamber containing a water-soluble polymer comprising thiol groups as described above, optionally provided in an aqueous solution, and a second chamber comprising a water-soluble metal salt as described above, optionally provided in an aqueous solution. The device may include a third chamber for combining the contents of the first and second chambers, or the device may be configured to permit the contents of the first chamber to be combined with the contents of the second chamber in one or more of the first chamber and the second chamber. The containers can be arranged in any manner within the housing, such as end-to-end, side-by-side, or in a surrounding arrangement. Other exemplary vascular closure devices are described, for example, in U.S. patent application Ser. No. 13/773,062, filed Feb. 21, 2013, the entire contents of which are incorporated herein by reference in the entirety. For example, the device can include a handle assembly that is attached to a delivery member, wherein the handle assembly comprises a plurality of chambers, including a first chamber containing a water-soluble polymer comprising thiol groups as described above, optionally provided in an aqueous solution, and a second chamber comprising a water-soluble metal salt as described above, optionally provided in an aqueous solution. In some embodiments, the hydrogel components remain separated from each other until being ejected from their respective chambers, such as during injection into the delivery member for delivery to the puncture site.

In some embodiments, a vascular closure device may be in the form of a syringe having a first compartment and a second compartment, wherein one compartment holds a water-soluble polymer comprising thiol groups as described herein (optionally provided in an aqueous solution), and the other compartment holds a water-soluble metal salt as described herein (optionally provided in an aqueous solution). In some embodiments, the water-soluble polymer and metal salt are combined upon injection into a subject, and the hydrogel forms in situ. In other embodiments, the water-soluble polymer and metal salt are combined prior to injection.

In some embodiments, the water-soluble polymer and metal salt are combined for a short time, for example about 1 to about 5 seconds, before being injected into the subject.

Uses and Methods

In some embodiments, the present disclosure relates to uses and methods relating to the hydrogels described herein.

In some embodiments, the present disclosure relates to a vascular sealing material comprising a hydrogel as described herein. In some embodiments, the present disclosure relates to vascular sealing methods comprising injecting an injectable hydrogel as described herein into a subject in need thereof at a site in need of vascular sealing.

In some embodiments, the present disclosure relates to a drug-delivery vehicle comprising a hydrogel described herein and a drug or other optional ingredient described above. In some embodiments, the present disclosure relates to therapeutic methods and/or drug delivery methods comprising injecting an injectable hydrogel as described herein into a subject in need thereof, wherein the hydrogel comprises a drug or other optional ingredient described above.

In some embodiments, the present disclosure relates to a tissue engineering material comprising a hydrogel as described herein. In specific embodiments, the hydrogel includes a component with tissue adhering or binding properties. In some embodiments, the present disclosure relates to tissue engineering methods comprising injecting an injectable hydrogel as described herein into a subject in need thereof at a site in need of tissue engineering. In specific embodiments, the hydrogel includes a component with tissue adhering or binding properties.

In accordance with any of these methods, the injectable hydrogel can be injected prior to or subsequent to hydrogel formation. That is, the injectable hydrogel can be injected by injecting a first component comprising a water-soluble polymer comprising thiol groups as described herein (optionally provided in an aqueous solution) substantially simultaneously with a second component comprising a water-soluble metal salt as described herein (optionally provided in an aqueous solution), or the injectable hydrogel can be injected by injecting the components after they have been combined.

EXAMPLES

Example 1: Gelation Time Observations for Hydrogels with Polyethylene Glycol Sulfhydryl and Gold Chloride at Ambient Temperature A 15 wt % solution of 4-armed polyethylene glycol sulfhydryl, MW 20,000 (P4SH-20; SunBio Inc.) was combined with a 0.0313 M gold chloride (Sigma-Aldrich) solution in a molar ratio of 3.8:1 (thiol:gold salt) at ambient temperature. The two components were combined using two syringes and a 3-way valve with two female luer lock ports for the syringes. The two solutions were allowed to mix for 3-5 seconds and a compact, transparent hydrogel was formed 1-5 seconds after mixing was completed. The results of gelation time observations of various PEG-based hydrogels are shown in Table 1. The PEG-based hydrogels generally gelled within 20 seconds.

TABLE 1

Composition and Gelation Time for PEG-based hydrogels.

| PEG-SH [no of arms] | Mw PEG-SH [g/mol] | $C_{PEG-SH}$ [wt %] | $C_{AuCl3}$ [M] | Molar ratio thiol:gold | Time to gel [sec] | Appearance |
|---|---|---|---|---|---|---|
| 2 | 3400 | 34 | 0.031 | 6.4:1 | 1-5 | Sticky |
| 4 | 20000 | 15 | 0.031 | 3.8:1 | 1-5 | Compact, elastic |
| 6 | 10000 | 15 | 0.063 | 2.9:1 | 1-5 | Loose, elastic |
| 4 | 10000 | 15 | 0.031 | 6.4:1 | 15-20 | Elastic |
| 4 | 10000 | 10 | 0.031 | 3.6:1 | 1-5 | Compact, elastic |

Example 2: Gelation Time Observations for Hydrogel with Polyethylene Glycol Sulfhydryl and Gold Chloride at Physiological Conditions A 15 wt % solution of 4-armed polyethylene glycol sulfhydryl, MW 10,000 (P4SH-10; SunBio Inc.) was combined with a 0.0313 M gold chloride (Sigma Aldrich) solution in a molar ratio of 2.6:1 between thiol and gold salt. The two components were combined using two syringes and a 3-way valve with two female luer lock ports for the syringes. The two solutions were allowed to mix for 3-5 seconds and the mixture was injected into a 0.067 M phosphate buffered saline solution with pH 7.4 at 37° C. A compact transparent hydrogel was formed 1-5 seconds after the mixing was completed.

The invention claimed is:

1. A method for producing a hydrogel, comprising combining
    (a) a first aqueous solution comprising from about 1 wt % to about 20 wt % water-soluble polymer, based on the weight of the first aqueous solution, wherein the water-soluble polymer comprises thiol groups, and wherein the molecular weight of the water-soluble polymer is about 10,000 g/mol or more, and
    (b) a second aqueous solution comprising from about 0.05 wt % to about 20 wt % water-soluble $AuCl_3$,
    wherein the molar ratio of the thiol groups of the water-soluble polymer in the first aqueous solution to gold atoms of the $AuCl_3$ in the second aqueous solution is from about 1:1 to about 5:1, and the volume ratio of the first aqueous solution to the second aqueous solution is from about 2:1 to about 4:1;
    thereby forming a hydrogel, wherein the hydrogel forms in five seconds or less.

2. The method of claim 1, wherein the water-soluble polymer comprises a polymer backbone and one or more branches and substituents.

3. The method of claim 2, wherein one or more of the backbone, the branches, or the substituents comprise a thiol group.

4. The method of claim 3, wherein the thiol group is attached at an end-cap position on one or more of the backbone, the branches, or the substituents.

5. The method of claim 1, wherein the water-soluble polymer comprises a polymer selected from the group consisting of polysaccharide; gelatin; cellulose; starch; lipids; albumin; collagen; polylysine; polyvinyl alcohol; polyvinyl pyrrolidone; polyethylene glycol; polypropylene glycol; polyacrylic compounds; methacrylic compounds; polyethylene imines; polysiloxane; polyacrylamides; polyethylene oxide; poly(2-acrylamido-2-methyl-1-propanesulfonic acid); copolymers of any of the foregoing; oligomers of lactic acid, glycolic acid, paradioxanone, caprolactone, trimethylene carbonate, or co-oligomers thereof; oligomeric esters; small molecules; and combinations of two or more thereof.

6. The method of claim 5, wherein the water-soluble polymer comprises a polyethylene glycol comprising at least 4 branches.

7. The method of claim 1, wherein the hydrogel is biodegradable.

8. The method of claim 1, wherein the water-soluble polymer comprises a polymer backbone.

* * * * *